United States Patent
Hammerberg

(10) Patent No.: US 9,546,219 B2
(45) Date of Patent: Jan. 17, 2017

(54) TREATMENT OF ALLERGIC DISEASES WITH RECOMBINANT ANTIBODIES

(71) Applicant: North Carolina State University, Raleigh, NC (US)

(72) Inventor: Bruce Hammerberg, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 14/374,679

(22) PCT Filed: Jan. 29, 2013

(86) PCT No.: PCT/US2013/023610
§ 371 (c)(1),
(2) Date: Jul. 25, 2014

(87) PCT Pub. No.: WO2013/119419
PCT Pub. Date: Aug. 15, 2013

(65) Prior Publication Data
US 2015/0010547 A1    Jan. 8, 2015

Related U.S. Application Data

(60) Provisional application No. 61/596,423, filed on Feb. 8, 2012.

(51) Int. Cl.
*A61K 39/395* (2006.01)
*C07K 16/42* (2006.01)
*A61K 47/48* (2006.01)
*A61K 39/00* (2006.01)

(52) U.S. Cl.
CPC ..... *C07K 16/4291* (2013.01); *A61K 47/48215* (2013.01); *A61K 2039/505* (2013.01); *C07K 2317/24* (2013.01); *C07K 2317/56* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,740,461 A | 4/1988 | Kaufman | |
| 4,816,567 A | 3/1989 | Cabilly et al. | |
| 4,912,040 A | 3/1990 | Kaufman et al. | |
| 4,946,778 A | 8/1990 | Ladner et al. | |
| 4,959,455 A | 9/1990 | Clark et al. | |
| 5,258,498 A | 11/1993 | Huston et al. | |
| 5,260,203 A | 11/1993 | Ladner et al. | |
| 5,530,101 A | 6/1996 | Queen et al. | |
| 5,585,089 A | 12/1996 | Queen et al. | |
| 5,693,761 A | 12/1997 | Queen et al. | |
| 5,693,762 A | 12/1997 | Queen et al. | |
| 5,760,185 A | 6/1998 | Kimachi et al. | |
| 5,959,177 A | 9/1999 | Hein et al. | |
| 6,040,498 A | 3/2000 | Stomp et al. | |
| 6,180,370 B1 | 1/2001 | Queen et al. | |
| 6,267,958 B1 | 7/2001 | Andya et al. | |
| 6,504,013 B1 | 1/2003 | Lawton et al. | |
| 6,841,659 B2 | 1/2005 | Turpen et al. | |
| 6,852,319 B2 | 2/2005 | Hein et al. | |
| 6,881,557 B2 | 4/2005 | Foote | |
| 7,247,711 B2 | 7/2007 | Benson et al. | |
| 7,261,890 B2 | 8/2007 | Krah, III et al. | |
| 7,470,773 B2 * | 12/2008 | Hammerberg | C07K 16/4291 530/387.1 |
| 7,736,648 B2 | 6/2010 | Kauvar et al. | |
| 7,781,647 B2 | 8/2010 | Bakker et al. | |
| 7,816,334 B2 | 10/2010 | Rice et al. | |
| 7,910,702 B2 | 3/2011 | Kav et al. | |
| 7,943,144 B2 | 5/2011 | Brown et al. | |
| 8,017,146 B2 | 9/2011 | Stefano et al. | |
| 8,025,898 B2 | 9/2011 | Houze et al. | |
| 8,036,738 B2 | 10/2011 | Sirkar et al. | |
| 8,041,421 B2 | 10/2011 | Birchall et al. | |
| 8,043,250 B2 | 10/2011 | Xu | |
| 8,043,830 B2 | 10/2011 | Barat et al. | |
| 8,067,005 B1 * | 11/2011 | Chapman | A61K 47/48215 424/136.1 |
| 8,071,333 B2 | 12/2011 | Giles-Komar et al. | |
| 8,076,456 B2 | 12/2011 | Mattson et al. | |
| 8,097,704 B2 | 1/2012 | Kim et al. | |

(Continued)

FOREIGN PATENT DOCUMENTS

DK    WO 2008106980 A2 *  9/2008  ......... C07K 16/1027
WO         WO 88/01649 A1    3/1988

OTHER PUBLICATIONS

Gunneriusson et al., J Bacteriol. Mar. 1996;178(5):1341-6.*
Rudikoff et al., Proc Natl Acad Sci U S A. Mar. 1982;79(6):1979-83.*
Janeway et al., Immunobiology, 3rd edition, Garland Publishing, 1997, pp. 3:1-3:11.*
Ames et al., Nat Rev Drug Discov. Mar. 2004;3(3):199-200.*
Corren et al., Ann Allergy Asthma Immunol. Sep. 2004;93(3):243-8.*

(Continued)

*Primary Examiner* — Michael Szperka
(74) *Attorney, Agent, or Firm* — Myers Bigel, P.A.

(57) ABSTRACT

Recombinant antibodies (including binding fragments thereof) that bind IgE are described, along with compositions and methods of using the same in the treatment of subjects in need thereof, including subjects afflicted with atopic dermatitis, allergic rhinitis, allergic conjunctivitis, urticaria, gastro-intestinal inflammation, or oral-pharyngeal inflammation. In some embodiments, the antibody is a single chain variable fragment (scFv) or a disulfide linked variable fragment (sdFv). In some embodiments, the subject is a dog, cat, or horse.

12 Claims, 1 Drawing Sheet

(56) References Cited

U.S. PATENT DOCUMENTS

| | | | |
|---|---|---|---|
| 8,101,175 B1 | 1/2012 | Croft et al. | |
| 8,101,184 B2 | 1/2012 | Li et al. | |
| 8,101,423 B2 | 1/2012 | Cunningham et al. | |
| 8,101,727 B2 | 1/2012 | Stover et al. | |
| 8,105,598 B2 | 1/2012 | Dimitrov et al. | |
| 2003/0190318 A1* | 10/2003 | Torigoe ............... | C07K 16/2866 424/143.1 |
| 2007/0161066 A1 | 7/2007 | Hammerberg | |
| 2009/0117124 A1 | 5/2009 | Liu et al. | |
| 2009/0252732 A1 | 10/2009 | Siadak et al. | |
| 2010/0040606 A1 | 2/2010 | Lantto et al. | |
| 2010/0040619 A1 | 2/2010 | Li et al. | |
| 2010/0061988 A1 | 3/2010 | Hansen | |
| 2010/0129380 A1 | 5/2010 | McKenzie et al. | |

OTHER PUBLICATIONS

International Search Report and Written Opinion, PCT/US2013/023610, mailed May 6, 2013.

Kavalier J. GenBank Accession S26468. Jul. 23, 1999. [Retrieved from the Internet Apr. 2, 2013: < http://www.ncbi.nim.nih.gov/protein/S26468>].

Bird et al. "Single-Chain Antigen-Binding Proteins" *Science* 242(4877):423-426 (1988).

De Graaf et al. "Expression of scFvs and scFv Fusion Proteins in Eukaryotic Cells" *Methods in Molecular Biology* 178:379-387 (2002).

Hammerberg et al. "Auto IgG anti-IgE and IgG X IgE immune complex presence and effects on ELISA-based quantitation of IgE in canine atopic dermatitis, demodectic acariasis and helminthiasis" *Veterinary Immunology and Immunopathology* 60:33-46 (1997).

Huston et al. "Protein engineering of antibody binding sites: Recovery of specific activity in an anti-digoxin single-chain Fv analogue produced in Escherichia coli" *Proceedings of the National Academy of Sciences* 85:5879-5883 (1988).

Jackson et al. "IgE is present on peripheral blood monocytes and B cells in normal dogs and dogs with atopic dermatitis but there is no correlation with serum IgE concentrations" *Veterinary Immunology and Immunopathology* 85:225-232 (2002).

Jones et al. "Replacing the complementarity-determining regions in a human antibody with those from a mouse" *Nature* 321:522-525 (1986).

Kostelny et al. "Formation of a Bispecific Antibody by the Use of Leucine Zippers" *The Journal of Immunology* 148(5):1547-1553 (1992).

Kriangkum et al. "Bispecific and bifunctional single chain recombinant antibodies" *Biomolecular Engineering* 18:31-40 (2001).

Lantto et al. "Chain Shuffling to Modify Properties of Recombinant Immunoglobulins" *Methods in Molecular Biology* 178:303-316 (2002).

Maniatis et al. "Regulation of Inducible and Tissue-Specific Gene Expression" *Science* 236(4806):1237-1245 (1987).

Marks et al. "By-Passing Immunization: Building High Affinity Human Antibodies by Chain Shuffling" *Bio/Technology* 10:779-783 (1992).

Morrison et al. "Chimeric human antibody molecules: Mouse antigen-binding domains with human constant region domains" *Proceedings of the National Academy of Sciences* 81:6851-6855 (1984).

Riechmann et al. "Reshaping human antibodies for therapy" *Nature* 332:323-327 (1988).

Songsivilai et al. "Bispecific antibody: a tool for diagnosis and treatment of disease" *Clinical & Experimental Immunology* 79:315-321 (1990).

Verhoeyen et al. "Reshaping Human Antibodies: Grafting an Antilysozyme Activity" *Science* 239(4847):1534-1536 (1988).

Voss et al. "The role of enhancers in the regulation of cell-type-specific transcriptional control" *Trends in Biochemical Sciences* 11:287-289 (1986).

Ward et al. "Binding activities of a repertoire of single immunoglobulin variable domains secreted from *Escherichia coli*" *Nature* 341:544-546 (1989).

* cited by examiner

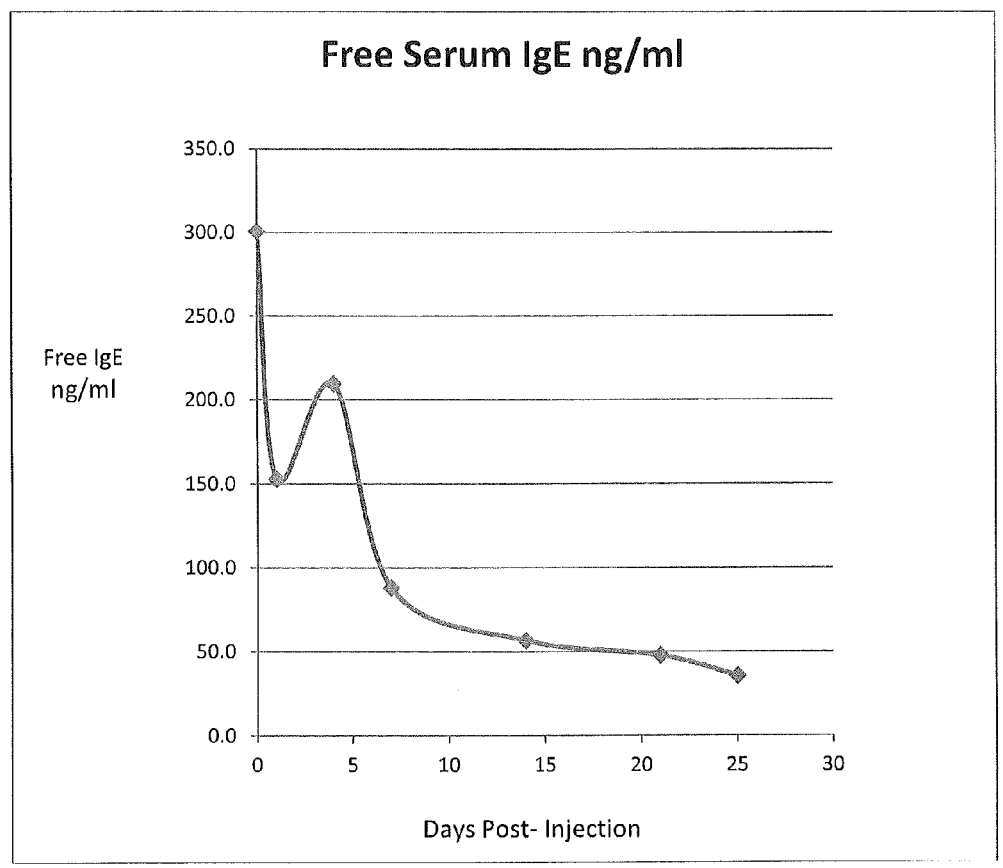

SEQUENCE LISTING

<160> NUMBER OF SEQ ID NOS: 13

<210> SEQ ID NO 1
<211> LENGTH: 327
<212> TYPE: DNA
<213> ORGANISM: Mus musculus
<220> FEATURE:
<221> NAME/KEY: CDS
<222> LOCATION: (1)..(327)

<400> SEQUENCE: 1

```
gac atc cag atg act cag tct cca gcc tcc cta tct gca tct gtg gga        48
Asp Ile Gln Met Thr Gln Ser Pro Ala Ser Leu Ser Ala Ser Val Gly
1               5                   10                  15 gaa act gtc acc atc aca tgt cga gca agt ggg aat att cac aat tat        96
Glu Thr Val Thr Ile Thr Cys Arg Ala Ser Gly Asn Ile His Asn Tyr
            20                  25                  30 tta gca tgg tat cag cag aaa cag gga aaa tct cct cag ctc ctg gtc       144
Leu Ala Trp Tyr Gln Gln Lys Gln Gly Lys Ser Pro Gln Leu Leu Val
        35                  40                  45 tat aat gca aaa acc tta gca gat agt gtg cca tca agg ttc agt ggc       192
Tyr Asn Ala Lys Thr Leu Ala Asp Ser Val Pro Ser Arg Phe Ser Gly
    50                  55                  60 agt gga tca gga aca caa ttt tct ctc aag atc aac agc ctg cag cct       240
Ser Gly Ser Gly Thr Gln Phe Ser Leu Lys Ile Asn Ser Leu Gln Pro
65                  70                  75                  80 gaa gat ttt ggg agt tat tac tgt caa cat ttt tgg agt act ccg tac       288
```

```
            Glu Asp Phe Gly Ser Tyr Tyr Cys Gln His Phe Trp Ser Thr Pro Tyr
                            85                  90                  95 acg ttc gga ggg ggg acc aag ctg gaa ata aaa cgg gct              327
            Thr Phe Gly Gly Gly Thr Lys Leu Glu Ile Lys Arg Ala
                        100                 105
```

<210> SEQ ID NO 2
<211> LENGTH: 109
<212> TYPE: PRT
<213> ORGANISM: Mus musculus

<400> SEQUENCE: 2

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Ser Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Trp Ser Thr Pro Tyr
                85                  90                  95

Thr Phe Gly Gly Gly Thr Lys Leu Glu Ile Lys Arg Ala
            100                 105
```

<210> SEQ ID NO 3
<211> LENGTH: 10
<212> TYPE: PRT
<213> ORGANISM: Mus musculus

<400> SEQUENCE: 3

```
Arg Ala Ser Gly Asn Ile His Asn Tyr Leu
1               5                   10
```

<210> SEQ ID NO 4
<211> LENGTH: 7
<212> TYPE: PRT
<213> ORGANISM: Mus musculus

<400> SEQUENCE: 4

```
Asn Ala Lys Thr Leu Ala Asp
1               5
```

<210> SEQ ID NO 5
<211> LENGTH: 7
<212> TYPE: PRT
<213> ORGANISM: Mus musculus

<400> SEQUENCE: 5

```
Phe Trp Ser Thr Pro Tyr Thr
1               5
```

<210> SEQ ID NO 6
<211> LENGTH: 360
<212> TYPE: DNA
<213> ORGANISM: Mus musculus
<220> FEATURE:
<221> NAME/KEY: CDS
<222> LOCATION: (1)..(360)

<400> SEQUENCE: 6

```
gag gtc cag ctg caa cag tca gga cct gag ctg gtg aag cct gga gcc    48
Glu Val Gln Leu Gln Gln Ser Gly Pro Glu Leu Val Lys Pro Gly Ala
1               5                   10                  15 tca atg aag att tcc tgc aag gct tct ggt tac tca atc act ggc tac    96
Ser Met Lys Ile Ser Cys Lys Ala Ser Gly Tyr Ser Ile Thr Gly Tyr
            20                  25                  30 acc ata cac tgg gtg aag cag agc cat gga aag aac ctt gag tgg att   144
Thr Ile His Trp Val Lys Gln Ser His Gly Lys Asn Leu Glu Trp Ile
        35                  40                  45 gga ctt att aat cct tac act ggt ggt att acc tac aac cag aac ttc   192
Gly Leu Ile Asn Pro Tyr Thr Gly Gly Ile Thr Tyr Asn Gln Asn Phe
    50                  55                  60 aag ggc aag gcc aca tta act gta gac aag tca tcc agc aca gcc tac   240
Lys Gly Lys Ala Thr Leu Thr Val Asp Lys Ser Ser Ser Thr Ala Tyr
65                  70                  75                  80 atg gag ctc ctc agt ctg aca tct gag gac tct gca gtc tat tac tgt   288
Met Glu Leu Leu Ser Leu Thr Ser Glu Asp Ser Ala Val Tyr Tyr Cys
                85                  90                  95 tca aga ggc ccc tat ggt aac ttc tat gct atg gac tac tgg ggt caa   336
Ser Arg Gly Pro Tyr Gly Asn Phe Tyr Ala Met Asp Tyr Trp Gly Gln
            100                 105                 110 gga acc tca gtc acc gtc tcc tca                                   360
Gly Thr Ser Val Thr Val Ser Ser
        115                 120
```

<210> SEQ ID NO 7
<211> LENGTH: 120
<212> TYPE: PRT
<213> ORGANISM: Mus musculus

<400> SEQUENCE: 7

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Ile Thr Gly Tyr
            20                  25                  30

Thr Ile His Trp Val Lys Gln Ser His Gly Lys Asn Leu Glu Trp Ile
        35                  40                  45

Gly Leu Ile Asn Pro Tyr Thr Gly Gly Ile Thr Tyr Asn Gln Asn Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ser Arg Gly Pro Tyr Gly Asn Phe Tyr Ala Met Asp Tyr Trp Gly Gln
            100                 105                 110

Gly Thr Ser Val Thr Val Ser Ser
        115                 120

<210> SEQ ID NO 8
<211> LENGTH: 5
<212> TYPE: PRT
<213> ORGANISM: Mus musculus

<400> SEQUENCE: 8

Gly Tyr Thr Ile His
1               5

<210> SEQ ID NO 9
<211> LENGTH: 20

```
<212> TYPE: PRT
<213> ORGANISM: Mus musculus

<400> SEQUENCE: 9

Leu Ile Asn Pro Tyr Thr Gly Gly Ile Thr Tyr Asn Gln Asn Phe Lys
1               5                   10                  15
Gly Lys Ala Thr
            20

<210> SEQ ID NO 10
<211> LENGTH: 11
<212> TYPE: PRT
<213> ORGANISM: Mus musculus

<400> SEQUENCE: 10

Gly Pro Tyr Gly Asn Phe Tyr Ala Met Asp Tyr
1               5                   10

<210> SEQ ID NO 11
<211> LENGTH: 18
<212> TYPE: PRT
<213> ORGANISM: Canis familiaris

<400> SEQUENCE: 11

Val Asp Gly Gln Lys Ala Thr Asn Ile Phe Pro Tyr Thr Ala Pro Gly
1               5                   10                  15
Thr Lys

<210> SEQ ID NO 12
<211> LENGTH: 744
<212> TYPE: DNA
<213> ORGANISM: Artificial
<220> FEATURE:
<223> OTHER INFORMATION: scFv cDNA fragment with codons optimized for
      tobacco plants
<220> FEATURE:
<221> NAME/KEY: CDS
<222> LOCATION: (7)..(738)

<400> SEQUENCE: 12 catatg gag gtt cag ctc cag cag agt ggt cca gag tta gtt aag cca         48
       Glu Val Gln Leu Gln Gln Ser Gly Pro Glu Leu Val Lys Pro
       1               5                   10 ggt gca tcc atg aag att tct tgt aaa gca tca ggt tat tcc att aca         96
Gly Ala Ser Met Lys Ile Ser Cys Lys Ala Ser Gly Tyr Ser Ile Thr
15                  20                  25                  30 ggt tac act ata cat tgg gtt aag caa tca cac gga aag aat ctt gag        144
Gly Tyr Thr Ile His Trp Val Lys Gln Ser His Gly Lys Asn Leu Glu
                35                  40                  45 tgg att gga ttg ata aac cca tac aca gga ggt atc act tac aac cag        192
Trp Ile Gly Leu Ile Asn Pro Tyr Thr Gly Gly Ile Thr Tyr Asn Gln
            50                  55                  60 aac ttc aag gga aaa gct act ctt aca gtt gat aag tct tca agt aca        240
Asn Phe Lys Gly Lys Ala Thr Leu Thr Val Asp Lys Ser Ser Ser Thr
65                  70                  75 gca tat atg gaa ctt ttg tcc ttg act tct gag gat tca gct gtg tat        288
Ala Tyr Met Glu Leu Leu Ser Leu Thr Ser Glu Asp Ser Ala Val Tyr
        80                  85                  90 tac tgt agt aga ggt cct tat gga aat ttc tac gct atg gat tat tgg        336
Tyr Cys Ser Arg Gly Pro Tyr Gly Asn Phe Tyr Ala Met Asp Tyr Trp
95                  100                 105                 110 gga caa ggt aca tct gtt act gtg tcc tct gga ggt gga ggt tct gga        384
Gly Gln Gly Thr Ser Val Thr Val Ser Ser Gly Gly Gly Gly Ser Gly
```

-continued

```
                        115                 120                 125
ggt gga ggt tca gga ggt gga ggt agt gat att caa atg aca cag tca    432
Gly Gly Gly Ser Gly Gly Gly Gly Ser Asp Ile Gln Met Thr Gln Ser
            130                 135                 140 cct gct tca ctt agt gca tcc gtt ggt gaa act gtg aca atc act tgc    480
Pro Ala Ser Leu Ser Ala Ser Val Gly Glu Thr Val Thr Ile Thr Cys
        145                 150                 155 aga gct tct gga aac ata cat aac tac tta gca tgg tac caa cag aag    528
Arg Ala Ser Gly Asn Ile His Asn Tyr Leu Ala Trp Tyr Gln Gln Lys
    160                 165                 170 cag ggt aaa tca cca cag tta ctc gtt tac aat gct aag aca ctt gca    576
Gln Gly Lys Ser Pro Gln Leu Leu Val Tyr Asn Ala Lys Thr Leu Ala
175                 180                 185                 190 gat agt gtg cct tcc agg ttt tct gga tca ggt agt gga act caa ttc    624
Asp Ser Val Pro Ser Arg Phe Ser Gly Ser Gly Ser Gly Thr Gln Phe
                195                 200                 205 tcc ctc aag att aat agt ctc cag cct gag gat ttt gga tct tat tac    672
Ser Leu Lys Ile Asn Ser Leu Gln Pro Glu Asp Phe Gly Ser Tyr Tyr
            210                 215                 220 tgt cag cac ttc tgg tct act cct tac aca ttt ggt ggt gga act aaa    720
Cys Gln His Phe Trp Ser Thr Pro Tyr Thr Phe Gly Gly Gly Thr Lys
        225                 230                 235 ctt gag ata aag aga tga ctcgag                                     744
Leu Glu Ile Lys Arg
    240
```

<210> SEQ ID NO 13
<211> LENGTH: 243
<212> TYPE: PRT
<213> ORGANISM: Artificial
<220> FEATURE:
<223> OTHER INFORMATION: Synthetic Construct

<400> SEQUENCE: 13

```
Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Ile Thr Gly Tyr
            20                  25                  30

Thr Ile His Trp Val Lys Gln Ser His Gly Lys Asn Leu Glu Trp Ile
        35                  40                  45

Gly Leu Ile Asn Pro Tyr Thr Gly Gly Ile Thr Tyr Asn Gln Asn Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ser Arg Gly Pro Tyr Gly Asn Phe Tyr Ala Met Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ala
    130                 135                 140

Ser Leu Ser Ala Ser Val Gly Glu Thr Val Thr Ile Thr Cys Arg Ala
145                 150                 155                 160

Ser Gly Asn Ile His Asn Tyr Leu Ala Trp Tyr Gln Gln Lys Gln Gly
                165                 170                 175

Lys Ser Pro Gln Leu Leu Val Tyr Asn Ala Lys Thr Leu Ala Asp Ser
            180                 185                 190
```

```
Val Pro Ser Arg Phe Ser Gly Ser Gly Ser Gly Thr Gln Phe Ser Leu
        195                 200                 205

Lys Ile Asn Ser Leu Gln Pro Glu Asp Phe Gly Ser Tyr Tyr Cys Gln
    210                 215                 220

His Phe Trp Ser Thr Pro Tyr Thr Phe Gly Gly Gly Thr Lys Leu Glu
225                 230                 235                 240

Ile Lys Arg
```

TREATMENT OF ALLERGIC DISEASES WITH RECOMBINANT ANTIBODIES

RELATED APPLICATIONS

This application is a 35 U.S.C. §371 national phase entry of PCT Application PCT/US2013/023610, filed Jan. 29, 2013, and published in English on Aug. 15, 2013, as International Publication No. WO 2013/119419, and which claims the benefit of U.S. Provisional Patent Application Ser. No. 61/596,423, filed Feb. 8, 2012, the disclosure of each of which is incorporated by reference herein in its entirety.

FIELD OF THE INVENTION

The present invention concerns compounds and compositions useful for treating IgE-related disorders in mammalian subjects, particularly veterinary subjects, along with methods of making and using the same.

BACKGROUND OF THE INVENTION

Treatment of chronic allergic diseases in dogs, often seen as recurring dermatitis, frequently results in less than optimal outcomes. When the disease can be linked to exposure to specific allergens, such house dust mites, desensitization injections can be effective in some individuals when carried out over an extended time; however, most cases are not resolved by desensitization and require a combination of allergen avoidance and anti-inflammatory drugs. The prolonged use of these drugs, such as corticosteroids, can result in severe side effects. These same challenges exist for human allergy suffers, but recently there has been a major breakthrough in the development of a new, safe and effective therapy using a monoclonal antibody that specifically binds and neutralizes human IgE that is responsible for activating inflammation-producing cells. This product is called XOLAIR® brand omalizumab (see, e.g., U.S. Pat. No. 6,267,958 example 2) and it has been used safely by millions of allergy patients for more than 5 years.

SUMMARY OF THE INVENTION

A first aspect of the invention is a recombinant antibody or binding fragment thereof, comprising: (i) a light chain (LC) variable region having at complementarity determining regions (CDRs) thereof at least one, two, or all three of the amino acid sequences of RASGNIHNYL (LC CDR1; SEQ ID NO:3); NAKTLAD (LC CDR2; SEQ ID NO:4); and FWSTPYT (LC CDR3; SEQ ID NO:5); and/or (ii) a heavy chain (HC) variable region having at complementarity determining regions (CDRs) thereof at least one, two, or all three of the amino acid sequences of: GYTIH (HC CDR1; SEQ ID NO:8); LINPYTGGITYNQNFKGKAT (HC CDR2; SEQ ID NO:9); and GPYGNFYAMDY (HC CDR3; SEQ ID NO:10).

In some embodiments, the antibody or binding fragment thereof specifically binds to canine IgE at the epitope corresponding to amino acids 146 to 162 thereof (VDGQKATNIFPYTAPGTK, SEQ ID NO:11).

In some embodiments, the antibody or binding fragment thereof binds to canine IgE at a dissociation constant ($K_d$) not greater than 50 nM, 10 nM, or 1 nM.

In some embodiments, the antibody or binding fragment thereof is a single chain variable fragment (scFv) or a disulfide linked variable fragment (sdFv).

In some embodiments, the antibody or binding fragment thereof is a chimeric antibody or binding fragment thereof.

In some embodiments, the antibody or binding fragment thereof further comprises a water soluble polyalkylene oxide group coupled thereto (e.g., is PEGylated).

A further aspect of the invention is a method of reducing free serum IgE levels in a mammalian subject in need thereof, comprising administering said subject an antibody as described herein or binding fragment thereof in an amount effective to reduce free serum IgE levels in said subject. For example, the subject may be afflicted with a condition such as atopic dermatitis, allergic rhinitis, allergic conjunctivitis, urticaria, gastro-intestinal inflammation, or oral-pharyngeal inflammation, with the antibody or binding fragment thereof being administered in a treatment-effective amount or amount effective to treat the condition.

A further aspect of the invention is a composition comprising an antibody as described herein or binding fragment thereof in a pharmaceutically acceptable carrier.

A further aspect of the invention is an antibody as described herein or binding fragment thereof for use in the preparation of a medicament for carrying out a method of any preceding claim.

Further aspects of the invention is a recombinant nucleic acid (e.g., in isolated and/or purified form) encoding an antibody as described herein, or a binding fragment thereof, along with host cells containing such a nucleic acid and expressing the encoded antibody or binding fragment thereof. Examples of such host cells include, but are not limited to, bacterial cells, yeast cells, mammalian cells (e.g., in culture), and plant cells (e.g., in vitro, in vivo or in planta).

A further aspect of the invention is a method of making a recombinant antibody as described herein, or binding fragment thereof, comprising: (a) maintaining a host cell as described herein under conditions in which the encoded antibody or binding fragment thereof is expressed; and then (b) collecting (directly or indirectly) that recombinant antibody or binding fragment thereof from the host cell (e.g., by lysing the cell; by collecting recombinant antibody secreted into media in which the cell is grown, etc.).

Utility.

Antibodies of the present invention are useful as therapeutic active agents for treating subjects to lower free IgE levels therein, including for the treatment of the disorders and diseases described herein below. In addition, humanized antibodies of the invention are useful as laboratory reagents for studying the mechanism of blocking Fc epsilon R1 binding to IgE in more detail, for the allosteric binding to IgE that the present invention demonstrating, using the greater array of reagents available for human IgE and Fe epsilon R1, which studies are in turn useful for the development of still more potential therapeutic agents for treating the conditions described herein.

The present invention is explained in greater detail in the drawings herein and the specification set forth below. The disclosures of all United States patent references cited herein are incorporated by reference herein in their entirety.

BRIEF DESCRIPTION OF THE DRAWINGS

FIG. 1 shows the decrease in serum free immunoglobulin E (IgE) in a dog treated with a monoclonal antibody of the invention.

DETAILED DESCRIPTION OF ILLUSTRATIVE EMBODIMENTS

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. See generally Li et al., *Treatment Methods Using Dkk-1 Antibodies*, U.S. Pat. No. 8,101,184 (Amgen).

As discussed in greater detail below, the present invention can be carried out in accordance with known techniques, or variations thereof that will be apparent to those skilled in the art. See, e.g., U.S. Pat. No. 8,101,184; see also U.S. Pat. Nos. 8,105,598; 8,101,727; 8,101,423; 8,101,175; and 8,097,704.

DEFINITIONS

Subjects with which the present invention is concerned are, in general, mammalian subjects, particularly veterinary subjects such as dogs, cats, and horses. The subjects may be of any gender and any age.

"Therapeutically effective amount" or "treatment effective amount" as used herein refers to the amount of an anti-IgE antibody determined to produce a therapeutic response in a mammal. Such therapeutically effective amounts are readily ascertained by one of ordinary skill in the art.

"Canine IgE" is known and described in, for example, U.S. Pat. Nos. 7,261,890 and 6,504,013.

"Antibody" as used herein refers to an intact immunoglobulin of any isotype, or a fragment thereof that can compete with the intact antibody for specific binding to the target antigen, and includes chimeric, humanized, caninized, equinized, felinized, fully human, fully canine, fully equine, fully feline, and bispecific antibodies. An intact antibody generally will comprise at least two full-length heavy chains and two full-length light chains, but in some instances may include fewer chains such as antibodies naturally occurring in camelids which may comprise only heavy chains. Antibodies according to the invention may be derived solely from a single source, or may be "chimeric," that is, different portions of the antibody may be derived from two different antibodies. For example, the CDR regions may be derived from a rat or murine source, while the framework region of the V region are derived from a different animal source, such as a human. The antibodies or binding fragments of the invention may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below.

"Light chain" as used herein includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains according to the invention include kappa chains and lambda chains.

"Heavy chain" includes a full-length heavy chain and fragments thereof having sufficient variable region sequence to confer binding specificity. A full-length heavy chain includes a variable region domain, $V_H$, and three constant region domains, $C_{H1}$, $C_{H2}$, and $C_{H3}$. The $V_H$ domain is at the amino-terminus of the polypeptide, and the $C_H$ domains are at the carboxyl-terminus, with the $C_{H3}$ being closest to the —COOH end. Heavy chains according to the invention may be of any isotype, including IgG (including IgG1, IgG2, IgG3 and IgG4 subtypes), IgA (including $IgA_1$ and $IgA_2$ subtypes), IgM and IgE.

"Immunologically functional fragment" (or simply "fragment") of an immunoglobulin chain, as used herein, refers to a portion of an antibody light chain or heavy chain that lacks at least some of the amino acids present in a full-length chain but which is capable of binding specifically to an antigen. Such fragments are biologically active in that they bind specifically to the target antigen and can compete with intact antibodies for specific binding to a given epitope. In one aspect of the invention, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of intact antibodies. Immunologically functional immunoglobulin fragments of the invention include, but are not limited to, Fab, Fab', F(ab')$_2$, Fv, domain antibodies and single-chain antibodies, and may be derived from any mammalian source, including but not limited to human, mouse, rat, camelid or rabbit. It is contemplated further that a functional portion of the inventive antibodies, for example, one or more CDRs, could be covalently bound to a second protein or to a small molecule to create a therapeutic agent directed to a particular target in the body, possessing bifunctional therapeutic properties, or having a prolonged serum half-life.

"Fab fragment" as used herein is comprised of one light chain and the CHI and variable regions of one heavy chain. The heavy chain of a Fab molecule cannot form a disulfide bond with another heavy chain molecule.

"Fc" region as used herein contains two heavy chain fragments comprising the C.sub.H1 and C.sub.H2 domains of an antibody. The two heavy chain fragments are held together by two or more disulfide bonds and by hydrophobic interactions of the CH3 domains.

"Fab' fragment" contains one light chain and a portion of one heavy chain that contains the V.sub.H domain and the C.sub.H1 domain and also the region between the C.sub.H1 and C.sub.H2 domains, such that an interchain disulfide bond can be formed between the two heavy chains of two Fab' fragments to form a F(ab').sub.2 molecule.

"F(ab')$_2$ fragment" contains two light chains and two heavy chains containing a portion of the constant region between the C.sub.H1 and C.sub.H2 domains, such that an interchain disulfide bond is formed between the two heavy chains. A F(ab').sub.2 fragment thus is composed of two Fab' fragments that are held together by a disulfide bond between the two heavy chains.

"Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference.

"Domain antibody" as used herein is an immunologically functional immunoglobulin fragment containing only the variable region of a heavy chain or the variable region of a light chain. In some instances, two or more V.sub.H regions are covalently joined with a peptide linker to create a bivalent domain antibody. The two V.sub.H regions of a bivalent domain antibody may target the same or different antigens.

"Bivalent antibody" as used herein comprises two antigen binding sites. In some instances, the two binding sites have the same antigen specificities. However, bivalent antibodies may be bispecific (see below).

"Multispecific antibody" as used herein is one that targets more than one antigen or epitope.

"Bispecific," "dual-specific" or "bifunctional" antibody as used herein is a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai & Lachmann (1990), Clin. Exp. Immunol. 79:315-321; Kostelny et al. (1992), J. Immunol. 148:1547-1553. The two binding sites of a bispecific antibody will bind to two different epitopes, which may reside on the same or different protein targets.

III. Antibodies and Immunologically Functional Fragments

As discussed below, a variety of selective binding agents useful for regulating the activity of IgE are provided. These agents include, for instance, antibodies and immunologically functional fragments thereof that contain an antigen binding domain (e.g., single chain antibodies, domain antibodies, immunoadhesions, and polypeptides with an antigen binding region) and specifically bind to a Canine IgE.

Variable Domains of Antibodies.

Also provided are antibodies that comprise a light chain variable region as described herein, and/or a heavy chain variable region as described herein CDRs of Antibodies.

The antibodies and immunological functional fragments that are provided can include one, two, three, four, five or all six of the CDRs listed herein. The heavy and light chain variable regions and the CDRs that are disclosed herein can be used to prepare any of the various types of immunologically functional fragments that are known in the art including, but not limited to, domain antibodies, Fab fragments, Fab' fragments, F(ab')₂ fragments, Fv fragments, single-chain antibodies, sdFvs, scFvs, etc.

Single-Chain Variable Fragments.

Single chain variable fragment (scFv) antibodies can be produced in accordance with known techniques or variations thereof that will be apparent to those skilled in the art. See generally U.S. Pat. No. 4,946,778 to Ladner et al. and U.S. Pat. No. 5,258,498 to Huston and Opperman; see also U.S. Pat. Nos. 8,097,704; 8,043,830; 7,943,144; 7,910,702; and 7,816,334.

Bispecific or Bifunctional Antibodies.

The antibodies that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann, 1990, Clin. Exp. Immunol. 79: 315-321; Kostelny et al., 1992, J. Immunol. 148: 1547-1553.

Chimeric, Humanized, Caninized, Equinized, and Felinized Antibodies.

Chimeric and humanized antibodies based upon the foregoing sequences are also provided. Monoclonal antibodies for use as therapeutic agents may be modified in various ways prior to use. One example is a "chimeric" antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., Proc. Natl. Acad. Sci. USA 81:6851-6855 (1985), which are hereby incorporated by reference. CDR grafting is described, for example, in U.S. Pat. Nos. 6,180,370, 5,693,762, 5,693,761, 5,585,089, and 5,530,101, which are all hereby incorporated by reference for all purposes.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the V region or selected CDRs from a rodent antibody often are grafted into a human antibody, replacing the naturally-occurring V regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089, and 5,693,762; Jones et al., 1986, Nature 321:522-25; Riechmann et al., 1988, Nature 332:323-27; Verhoeyen et al., 1988, Science 239: 1534-36).

Caninized, equinized, and felinized antibodies are known, and are made in like manner as described in connection with humanized antibodies above. See, e.g., U.S. Pat. Nos. 8,076,456; 7,261,890; 6,881,557; 6,504,013; 5,760,185; and US Patent Application Pub. No. US 2010/0061988.

In one aspect of the invention, the CDRs of the light and heavy chain variable regions of the antibodies provided herein are grafted to framework regions (FRs) from antibodies from the same, or a different, phylogenetic species. For example, the CDRs of the light and heavy chain variable regions of the antibody can be grafted to consensus human, canine, equine, or feline FRs. To create consensus FRs, FRs from several heavy chain or light chain amino acid sequences of the desired species may be aligned to identify a consensus amino acid sequence. In other embodiments, the FRs of the antibody heavy chain or light chain are replaced with the FRs from a different heavy chain or light chain.

In one aspect of the invention, rare amino acids in the FRs of the heavy and light chains of anti-Canine IgE antibody are not replaced, while the rest of the FR amino acids are replaced. A "rare amino acid" is a specific amino acid that is in a position in which this particular amino acid is not usually found in an FR. Alternatively, the grafted variable regions from the antibody may be used with a constant region that is different from the constant region of. In other embodiments of the invention, the grafted variable regions are part of a single chain Fv antibody.

Nucleic Acids.

Nucleic acids that encode one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acids can be any length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

In another aspect, the present invention provides vectors comprising a nucleic acid encoding a polypeptide of the invention or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors, Tumor-inducing (Ti) plasmids, ballistic particles carrying recombinant nucleic acids, etc. The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, *E. coli*) or eukaryotic cell (for example, yeast, insect, plant, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Preparation of Antibodies.

The single chain antibodies that are provided may be formed by linking heavy and light chain variable domain (Fv region) fragments via an amino acid bridge (short peptide linker), resulting in a single polypeptide chain. Such single-chain Fvs (scFvs) may be prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains. By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87.

Antibodies provided herein that are of one subclass can be changed to antibodies from a different subclass using subclass switching methods. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., 2002, Methods Mol. Biol. 178:303-16.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, BioTechnology, 10:779.

Conservative modifications may be made to the heavy and light chains described in Table 1 (and corresponding modifications to the encoding nucleic acids) to produce an anti-Canine IgE antibody having functional and biochemical characteristics. Methods for achieving such modifications are described above.

Antibodies and functional fragments thereof according to the invention may be further modified in various ways. For example, if they are to be used for therapeutic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody or fragment thereof. Another useful fusion partner for the inventive antibodies or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antibodies and fragments described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a normative residue that has little or no effect on the polarity or charge of the amino acid residue at that position. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibodies provided herein, or to increase or decrease the affinity of these antibodies for human Canine IgE or for modifying the binding affinity of other anti-Canine IgE antibodies described herein.

Expression of Anti-Canine IgE Antibodies.

The anti-Canine IgE antibodies and immunological functional fragments or binding fragments thereof can be prepared by any of a number of conventional techniques. For example, anti-Canine IgE antibodies may be produced by recombinant expression systems, using any technique known in the art. See, for example, Monoclonal Antibodies, Hybridomas: A New Dimension in Biological Analyses, Kennet et al. (eds.) Plenum Press, New York (1980): and Antibodies: A Laboratory Manual, Harlow and Lane (eds.), Cold Spring Harbor Laboratory Press, Cold Spring Harbor, N.Y. (1988).

Antibodies of the present invention and binding fragments thereof can be expressed in hybridoma cell lines or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216, 4,912,040, 4,740,461, and 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs of the invention typically comprise a nucleic acid molecule encoding a polypeptide comprising one or more of the following: a heavy chain constant region; a heavy chain variable region; a light chain constant region; a light chain variable region; one or more CDRs of the light or heavy chain of the anti-Canine IgE antibody. These nucleic acid sequences are inserted into an appropriate expression vector using standard ligation techniques. In one embodiment, the canine, equine, feline, or human antibody heavy or light chain constant region is appended to the C-terminus of the Canine IgE-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase.

Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Optionally, the vector may contain a "tag"-encoding sequence, that is, an oligonucleotide molecule located at the 5' or 3' end of the coding sequence, the oligonucleotide sequence encoding polyHis, or another "tag" for which commercially available antibodies exist, such as FLAG®™, HA (hemaglutinin from influenza virus), or myc. The tag is typically fused to the antibody protein upon expression, and can serve as a means for affinity purification of the antibody from the host cell. Affinity purification can be accomplished, for example, by column chromatography using antibodies against the tag as an affinity matrix. Optionally, the tag can subsequently be removed from the purified antibody polypeptide by various means such as using certain peptidases for cleavage.

Flanking sequences in the expression vector may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, column chromatography, or other methods known to the skilled artisan. The selection of suitable enzymes to accomplish this purpose will be readily apparent to those skilled in the art.

An origin of replication is typically a part of prokaryotic expression vectors, particularly those purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 is suitable for most gram-negative bacteria and various origins (e.g., SV40, polyoma, adenovirus, vesicular stomatitis virus (VSV), or papillomaviruses such as HPV or BPV) are useful for cloning vectors in mammalian cells. Generally, a mammalian origin of replication is not needed for mammalian expression vectors (for example, the SV40 origin is often used only because it contains the early promoter).

The expression and cloning vectors of the present invention will typically contain a promoter that is recognized by the host organism and operably linked to nucleic acid encoding the anti-Canine IgE antibody or immunologically functional fragment thereof. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continuous gene product production; that is, there is little or no experimental control over gene expression. A large number of promoters, recognized by a variety of potential host cells, are well known. A suitable promoter is operably linked to the DNA encoding anti-Canine IgE antibody by removing the promoter from the source DNA by restriction enzyme digestion or amplifying the promoter by polymerase chain reaction and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Particular promoters useful in the practice of the recombinant expression vectors of the invention include, but are not limited to: the SV40 early promoter region; the CMV promoter; the promoter contained in the 3' long terminal repeat of Rous sarcoma virus; the herpes thymidine kinase promoter; the regulatory sequences of the metallothionine; prokaryotic expression vectors such as the beta-lactamase promoter; or the tac promoter. Also available for use are the following animal transcriptional control regions, which exhibit tissue specificity and have been utilized in transgenic animals: the elastase I gene control region that is active in pancreatic acinar cells; the insulin gene control region that is active in pancreatic beta cells; the mouse mammary tumor virus control region that is active in testicular, breast, lymphoid and mast cells; the albumin gene control region that is active in; the alpha-feto-protein gene control region that is active in liver; the alpha 1-antitrypsin gene control region that is active in the liver; the beta-globin gene control region that is active in myeloid cells; the myelin basic protein gene control region that is active in oligodendrocyte cells in the brain; the myosin light chain-2 gene control region that is active in skeletal muscle; the gonadotropic releasing hormone gene control region that is active in the hypothalamus; and the immunoglobulin gene control region that is active in lymphoid.

An enhancer sequence may be inserted into the vector to increase the transcription in higher eukaryotes of a nucleic acid encoding an anti-Canine IgE antibody or immunologically functional fragment thereof of the present invention. Enhancers are cis-acting elements of DNA, usually about 10-300 base pairs in length, that act on promoters to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). An enhancer sequence from a virus also can be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically placed at a site 5' to the promoter.

In expression vectors, a transcription termination sequence is typically located 3' of the end of a polypeptide-coding region and serves to terminate transcription. A transcription termination sequence used for expression in prokaryotic cells typically is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes used in expression vectors encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Examples of selectable markers include the kanamycin resistance gene, the ampicillin resistance gene and the tetracycline resistance gene. A bacterial neomycin resistance gene can also be used for selection in both prokaryotic and eukaryotic host cells.

Other selection genes can be used to amplify the gene that will be expressed. Amplification is a process whereby genes that cannot in single copy be expressed at high enough levels to permit survival and growth of cells under certain selection conditions are reiterated in tandem within the chromosomes of successive generations of recombinant cells. Examples of suitable amplifiable selectable markers for mammalian cells include dihydrofolate reductase (DHFR) and promoterless thymidine kinase. In the use of these markers mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively increased, thereby permitting survival of only those cells in which the selection gene has been amplified. Under these circumstances, DNA adjacent to the selection gene, such as DNA encoding an antibody of the invention, is co-amplified with the selection gene. As a result, increased quantities of anti-Canine IgE polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, for example where glycosylation is desired in a eukaryotic host cell expression system, various presequences can be manipulated to improve glycosylation or yield. For example, the peptidase cleavage site of a particular signal peptide can be altered, or pro-sequences added, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated yet active form of the desired polypeptide, if the enzyme cuts at such area within the mature polypeptide.

Where a commercially available expression vector lacks some of the desired flanking sequences as described above, the vector can be modified by individually ligating these sequences into the vector. After the vector has been chosen and modified as desired, a nucleic acid molecule encoding an anti-Canine IgE antibody or immunologically functional fragment thereof is inserted into the proper site of the vector.

The completed vector containing sequences encoding the inventive antibody or immunologically functional fragment thereof is inserted into a suitable host cell for amplification and/or polypeptide expression. The transformation of an expression vector for an anti-Canine IgE antibody immunologically functional fragment thereof into a selected host cell may be accomplished by well-known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan.

The transformed host cell, when cultured under appropriate conditions, synthesizes an anti-Canine IgE antibody or functional fragment thereof that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), such as Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, the best cell line for expressing a particular DNA construct may be selected by testing various cell lines to determine which ones have the highest levels of expression levels and produce antibodies with constitutive Canine IgE binding properties.

In addition to the foregoing, systems for the production of transgenic plants that produce transgenic antibodies, and from which the antibodies are collected, are known and can also be used to carry out the present invention. Examples of such plants, methods of making such plants, and methods of using such plants for the production and collection of antibodies are described in, for example, U.S. Pat. Nos. 8,071,333; 7,781,647; 7,736,648; 7,247,711; 6,852,319 6,841,659; 6,040,498; and 5,959,177.

Pharmaceutical Compositions and Methods of Use.

A. Exemplary Formulations.

In certain embodiments, the invention also provides compositions comprising the subject anti-Canine IgE antibodies or immunologically functional fragments thereof together with one or more of the following: a pharmaceutically acceptable diluent; a carrier; a solubilizer; an emulsifier; a preservative; and/or an adjuvant. Such compositions may contain an effective amount of the anti-Canine IgE antibody or immunologically functional fragment thereof. Thus, the use of the antibodies and immunologically active fragments that are provided herein in the preparation of a pharmaceutical composition or medicament is also included. Such compositions can be used in the treatment of a variety of diseases such as listed below in the section on exemplary utilities.

Acceptable formulation components for pharmaceutical preparations are nontoxic to recipients at the dosages and concentrations employed. In addition to the antibodies and immunologically functional fragments that are provided, compositions according to the invention may contain components for modifying, maintaining or preserving, for example, the pH, osmolarity, viscosity, clarity, color, isotonicity, odor, sterility, stability, rate of dissolution or release, adsorption or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. The primary vehicle or carrier in a pharmaceutical composition may be either aqueous or non-aqueous in nature. Suitable vehicles or carriers for such compositions include water for injection, physiological saline solution or artificial cerebrospinal fluid, possibly supplemented with other materials common in compositions for parenteral administration. Neutral buffered saline or saline mixed with serum albumin are further exemplary vehicles. Compositions comprising anti-Canine IgE antibodies or immunologically functional fragments thereof may be prepared for storage by mixing the selected composition having the desired degree of purity with optional formulation agents in the form of a lyophilized cake or an aqueous solution. Further, the anti-Canine IgE antibodies or immunologically functional fragments thereof may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

A pharmaceutical composition may involve an effective quantity of anti-Canine IgE antibodies or immunologically functional fragments thereof in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert materials, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are in the form of sustained- or controlled-delivery formulations. Techniques for formulating a variety of other sustained- or controlled-delivery means, such as liposome carriers, bioerodible microparticles or porous beads and depot injections can be. Sustained-release preparations may include semipermeable polymer matrices in the form of shaped articles, e.g. films, or microcapsules, polyesters, hydrogels, polylactides, copolymers of L-glutamic acid and gamma ethyl-L-glutamate, poly(2-hydroxyethyl-methacrylate), ethylene vinyl acetate or poly-D(−)-3-hydroxybutyric acid. Sustained release compositions may also include liposomes, which can be prepared by any of several methods known in the art.

The pharmaceutical composition to be used for in vivo administration typically is sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The composition may be formulated for transdermal delivery, optionally with the inclusion of microneedles, microprojectiles, patches, electrodes, adhesives, backings, and/or packaging, or formulations for jet delivery, in accordance with known techniques. See, e.g., U.S. Pat. Nos. 8,043,250; 8,041,421; 8,036,738; 8,025,898; 8,017,146.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The present invention provides kits for producing a multi-dose or single-dose administration units. For example, kits according to the invention may each contain both a first container having a dried protein and a second container having an aqueous diluent, including for example single and multi-chambered pre-filled syringes (e.g., liquid syringes, lyosyringes or needle-free syringes).

The pharmaceutical compositions of the invention can be delivered parenterally, typically by injection. Injections can be intraocular, intraperitoneal, intraportal, intramuscular, intravenous, intrathecal, intracerebral (intra-parenchymal), intracerebroventricular, intraarterial, intralesional, perilesional or subcutaneous. Eye drops can be used for intraocular administration. In some instances, injections may be localized to the vicinity of a particular bone or bones to which the treatment is targeted. For parenteral administration, the antibodies may be administered in a pyrogen-free, parenterally acceptable aqueous solution comprising the desired anti-Canine IgE antibodies or immunologically functional fragments thereof in a pharmaceutically acceptable vehicle. A particularly suitable vehicle for parenteral injection is sterile distilled water in which the anti-Canine IgE antibodies or immunologically functional fragments thereof are formulated as a sterile, isotonic solution, properly preserved.

Pharmaceutical compositions comprising the subject anti-Canine IgE antibodies and functional fragments thereof may be administered by bolus injection or continuously by infusion, by implantation device, sustained release systems or other means for accomplishing prolonged release. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous release. The preparation may be formulated with agent, such as injectable microspheres, bio-erodible particles, polymeric compounds (such as polylactic acid; polyglycolic acid; or copoly(lactic/glycolic) acid (PLGA), beads or liposomes, that can provide controlled or sustained release of the product which may then be delivered via a depot injection. Formulation with hyaluronic acid has the effect of promoting sustained duration in the circulation.

The subject compositions comprising an anti-Canine IgE antibody or functional fragment thereof may be formulated for inhalation. In these embodiments, an anti-Canine IgE antibody is formulated as a dry powder for inhalation, or anti-Canine IgE antibody inhalation solutions may also be formulated with a propellant for aerosol delivery, such as by nebulization.

Certain pharmaceutical compositions of the invention can be delivered through the digestive tract, such as orally. The subject anti-Canine IgE antibodies or immunologically functional fragments thereof that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the anti-Canine IgE antibody or functional fragment thereof. For oral administration, modified amino acids may be used to confer resistance to digestive enzymes. Diluents, flavorings, low melting point waxes, vegetable oils, lubricants, suspending agents, tablet disintegrating agents, and binders may also be employed.

The subject compositions comprising anti-Canine IgE antibodies or immunologically functional fragments thereof also may be used ex vivo. In such instances, cells, tissues or organs that have been removed from the patient are exposed to or cultured with the anti-Canine IgE antibody. The cultured cells may then be implanted back into the patient or a different patient or used for other purposes.

In certain embodiments, anti-Canine IgE antibodies or immunologically functional fragments thereof can be delivered by implanting certain cells that have been genetically engineered, using methods such as those described herein, to express and secrete the polypeptide. Such cells may be animal or human cells, and may be autologous, heterologous, or xenogenic, or may be immortalized. In order to decrease the chance of an immunological response, the cells may be encapsulated to avoid infiltration of surrounding tissues. Encapsulation materials are typically biocompatible, semi-permeable polymeric enclosures or membranes that allow the release of the protein product(s) but prevent the destruction of the cells by the patient's immune system or by other detrimental factors from the surrounding tissues.

B. Conditions for Treatment.

Subjects to be treated by the methods and compositions of the present invention include any afflicted with a disorder or condition in which reduction of free IgE levels would be beneficial. Examples include, but are not limited to, atopic dermatitis, allergic rhinitis, allergic conjunctivitis, urticaria, gastro-intestinal inflammation, and oral-pharyngeal inflammation.

C. Dosage.

The pharmaceutical compositions that are provided can be administered for prophylactic and/or therapeutic treatments. An "effective amount" refers generally to an amount that is a sufficient, but non-toxic, amount of the active ingredient (i.e., an anti-Canine IgE antibody or immunologically functional fragment thereof) to achieve the desired effect, which is a reduction or elimination in the severity and/or frequency of symptoms and/or improvement or remediation of damage. A "therapeutically effective amount" refers to an amount that is sufficient to remedy a disease state or symptoms, or otherwise prevent, hinder, retard or reverse the progression of a disease or any other undesirable symptom. A "prophylactically effective amount" refers to an amount that is effective to prevent, hinder or retard the onset of a disease state or symptom.

In general, toxicity and therapeutic efficacy of the antibody or fragment can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

The data obtained from cell culture and/or animal studies can be used in formulating a range of dosages for subjects for treatment. The dosage of the active ingredient typically lines within a range of circulating concentrations that include the $ED_{50}$ with little or no toxicity. The dosage can vary within this range depending upon the dosage form employed and the route of administration utilized.

The effective amount of a pharmaceutical composition comprising anti-Canine IgE antibodies or immunologically functional fragments thereof to be employed therapeutically or prophylactically will depend, for example, upon the therapeutic context and objectives. One skilled in the art will appreciate that the appropriate dosage levels for treatment, according to certain embodiments, will thus vary depending, in part, upon the molecule delivered, the indication for which the anti-Canine IgE antibody is being used, the route of administration, and the size (body weight, body surface or organ size) and/or condition (the age and general health) of the subject. A clinician may titer the dosage and modify the route of administration to obtain the optimal therapeutic effect. Typical dosages range from about 10 or 100 ug/Kg, or 500 or 1 mg/Kg, up to about 50 or 100 mg/Kg subject body weight, or more.

The dosing frequency will depend upon the pharmacokinetic parameters of the anti-Canine IgE antibody or immunologically functional fragment thereof in the formulation. For example, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Treatment may be continuous over time or intermittent. Further refinement of the appropriate dosage is routinely made by those of ordinary skill in the art and is within the ambit of tasks routinely performed by them. Appropriate dosages may be ascertained through use of appropriate dose-response data.

To treat a disorder characterized by abnormal or excess expression of Canine IgE, a composition comprising the subject anti-Canine IgE antibodies or immunologically functional fragments thereof may be administered to the patient in an amount and for a time sufficient to induce a sustained improvement in at least one indicator that reflects the severity of the disorder. An improvement is considered "sustained" if the patient exhibits the improvement on at least two occasions separated by at least one to seven days, or in some instances one to six weeks. The appropriate interval will depend to some extent on what disease condition is being treated; it is within the purview of those skilled in the art to determine the appropriate interval for determining whether the improvement is sustained. The degree of improvement is determined based on signs or symptoms, and may also employ questionnaires that are administered to the patient, such as quality-of-life questionnaires.

Kits

Kits that include an antibody or immunologically functional fragment or a pharmaceutical composition as described herein are also provided. Some kits include such an antibody, fragment or composition in a container (e.g., vial or ampule), and may also include instructions for use of the antibody or fragment in the various methods disclosed above. The antibody, fragment or composition can be in various forms, including, for instance, as part of a solution or as a solid (e.g., lyophilized powder). The instructions may include a description of how to prepare (e.g., dissolve or resuspend) the antibody or fragment in an appropriate fluid and/or how to administer the antibody or fragment for the treatment of the diseases described.

The kits may also include various other components, such as buffers, salts, complexing metal ions and other agents described above in the section on pharmaceutical compositions. These components may be included with the antibody or fragment or may be in separate containers. The kits may also include other therapeutic agents for administration with the antibody or fragment. Examples of such agents include, but are not limited to, agents to treat the disorders or conditions described above.

The following examples are provided solely to illustrate certain aspects of the antibodies, fragments and compositions that are provided herein and thus should not be construed to limit the scope of the claimed invention.

EXAMPLE 1

In Vitro and Preliminary In Vivo Studies

Mouse monoclonal antibody 5.91 (mAb 5.91) was selected for extensive characterization from a panel of monoclonal antibodies made against canine IgE (Hammerberg, U.S. Pat. No. 7,470,773 (2008). This monoclonal binds canine IgE expressed on the surface of dog B cells committed to IgE production and binds B cells expressing the low affinity IgE binding receptor, CD23, occupied by IgE, as well as dendritic cells and basophils expressing the high affinity receptor for the epsilon chain of IgE, occupied by IgE in peripheral circulation (Jackson, Orton and Hammerberg, *Vet Immunol. Immunopathol.* 85, 225-232 (2002)). This is the same binding profile shown by the human IgE-binding omalizumab.

More recently we have found that mAb 5.91 blocks the binding of biotinylated canine×mouse heterohybridoma IgE to canine C2 mast cells in vitro and to circulating monocytes and B cells in whole blood samples. In this experiment mAb 5.91 was incubated with biotinylated canine IgE in phosphate buffered saline pH 7.6 for 30 minutes at room temperature before the addition of peripheral blood leukocytes that were pre-washed with lactic acid saline to remove endogenously bound IgE. After a further incubation at room temperature for 60 minutes the binding of biotinylated IgE was detected by flow cytometry with avidin labeled FITC. Yet mast cells activated with IgE are not bound by mAb 5.91 and do not degranulate when exposed to mAb 5.91.

Similarly, intradermal injection of mAb 5.91 at concentrations ranging from 0.01 to 10 mg/ml did not cause wheal and flare responses in dogs having a wide range of serum IgE levels. Monoclonal antibody 5.91 attached to sepharose beads has been used to affinity purify IgE and IgE×IgG complexes from the serum of dogs, demonstrating its ability to bind with high affinity circulating IgE at an epitope not routinely recognized by naturally occurring IgG auto-anti IgE antibodies (Hammerberg et al, *Vet. Immunol. Immunopathol.* 60, 33-46 (1997)).

EXAMPLE 2

In Vivo Activity of Monoclonal Antibody 5.91

This example shows the decrease in serum "free IgE" in a single 10 Kg beagle dog injected subcutaneously once at day 0 with 30 mg of mouse monoclonal antibody 5.91.

Blood was collected for serum just before injection and at 1, 4, 7, 14, 21 and 25 days post-injection. The ELISA for measuring "free IgE" was conducted with a rabbit IgG anti-canine IgE trapping antibody and recombinant human High Affinity IgE Receptor (Fc ε RI) labeled with biotin and detected with streptavidin peroxidase. Data is given in FIG. 1.

EXAMPLE 3

Cloning of MAb 5.91 Light Chain Variable Region (VR)

An RNA template was first prepared. Then, using a first set of PCR primers, VL-CK was successfully cloned. By DNA sequencing of VL DNA, the VL nucleotide and amino acid sequences were determined, and are given in Table 1.

TABLE 1

Sequence of VL

DNA (5' to 3'):
(SEQ ID NO: 1)
gacatccagatgactcagtctccagcctccctatctgcatctgtg ggagaaactgtcaccatcacatgtcgagcaagtgggaatattcac aattatttagcatggtatcagcagaaacagggaaaatctcctcag ctcctggtctataatgcaaaaaccttagcagatagtgtgccatca aggttcagtggcagtggatcaggaacacaattttctctcaagatc aacagcctgcagcctgaagattttgggagttattactgtcaacat ttttggagtactccgtacacgttcggaggggggaccaagctggaa ataaaacgggct Protein:
(SEQ ID NO: 2)
DIQMTQSPASLSASVGETVTITCRASGNIHNYLAWYQQKQGKSPQ

LLVYNAKTLADSVPSRFSGSGSGTQFSLKINSLQPEDFGSYYCQH

FWSTPYTFGGGTKLEIKRA

In Table 1, the CDRs are shown underlined. These three CDRs are:

CDR1:
(SEQ ID NO: 3)
RASGNIHNYL

CDR2:
(SEQ ID NO: 4)
NAKTLAD;
and

CDR3:
(SEQ ID NO: 5)
FWSTPYT.

EXAMPLE 4

Cloning of MAb 5.91 Heavy Chain Variable Region (VH)

To amplify VH CH1, four pair of primers were found that lead to specific amplification of one VH sequence. The sequence of VH is shown in Table 2.

TABLE 2 sequence of VH

DNA (5' to 3'):
(SEQ ID NO: 6)
gaggtccagctgcaacagtcaggacctgagctggtgaagcctgga gcctcaatgaagatttcctgcaaggcttctggttactcaatcact ggctacaccatacactgggtgaagcagagccatggaaagaacctt gagtggattggacttattaatccttacactggtggtattacctac aaccagaacttcaagggcaaggccacattaactgtagacaagtca tccagcacagcctacatggagctcctcagtctgacatctgaggac TABLE 2-continued sequence of VH tctgcagtctattactgttcaagaggccccctatggtaacttctat gctatggactactggggtcaaggaacctcagtcaccgtctcctca Protein:
(SEQ ID NO: 7)
EVQLQQSGPELVKPGASMKISCKASGYSITGYTIHWVKQSHGKNL

EWIGLINPYTGGITYNQNFKGKATTVDKSSSTAYMELLSLTSED

SAVYYCSRGPYGNFYAMDYWGQGTSVTVSS

In Table 2, CDRs are again shown underlined. These three CDRs are:

CDR1':
(SEQ ID NO: 8)
GYTIH;

CDR2':
(SEQ ID NO: 9)
LINPYTGGITYNQNFKGKAT;
and

CDR3':
(SEQ ID NO: 10)
GPYGNFYAMDY.

EXAMPLE 5

Preparation of Single Chain Variable Fragment (scFv)

An scFv cDNA fragment of the foregoing is prepared as shown in Table 3, with the codons optimized for tobacco plants (SEQ ID NO:12). The fragment is inserted in a pBR322 plasmid for subsequent insertion into tobacco plants for expression of the recombinant scFv antibody (SEQ ID NO:13).

TABLE 3

Sequence of T-5.91 scFv (nico)

NdeI
~~~~~~~

```
          E   V   Q   L   Q   Q   S   G   P   E   L   V   K   P   G   A   S   M
CAT ATG GAG GTT CAG CTC CAG CAG AGT GGT CCA GAG TTA GTT AAG CCA GGT GCA TCC ATG
GTA TAC CTC CAA GTC GAG GTC GTC TCA CCA GGT CTC AAT CAA TTC GGT CCA CGT AGG TAC

K   I   S   C   K   A   S   G   Y   S   I   T   G   Y   T   I   H   W   V   K
AAG ATT TCT TGT AAA GCA TCA GGT TAT TCC ATT ACA GGT TAC ACT ATA CAT TGG GTT AAG
TTC TAA AGA ACA TTT CGT AGT CCA ATA AGG TAA TGT CCA ATG TGA TAT GTA ACC CAA TTC

Q   S   H   G   K   N   L   E   W   I   G   L   I   N   P   Y   T   G   G   I
CAA TCA CAC GGA AAG AAT CTT GAG TGG ATT GGA TTG ATA AAC CCA TAC ACA GGA GGT ATC
GTT AGT GTG CCT TTC TTA GAA CTC ACC TAA CCT AAC TAT TTG GGT ATG TGT CCT CCA TAG

T   Y   N   Q   N   F   K   G   K   A   T   L   T   V   D   K   S   S   S   T
ACT TAC AAC CAG AAC TTC AAG GGA AAA GCT ACT CTT ACA GTT GAT AAG TCT TCA AGT ACA
TGA ATG TTG GTC TTG AAG TTC CCT TTT CGA TGA GAA TGT CAA CTA TTC AGA AGT TCA TGT

A   Y   M   E   L   L   S   L   T   S   E   D   S   A   V   Y   Y   C   S   R
GCA TAT ATG GAA CTT TTG TCC TTG ACT TCT GAG GAT TCA GCT GTG TAT TAC TGT AGT AGA
CGT ATA TAC CTT GAA AAC AGG AAC TGA AGA CTC CTA AGT CGA CAC ATA ATG ACA TCA TCT

G   P   Y   G   N   F   Y   A   M   D   Y   W   G   Q   G   T   S   V   T   V
GGT CCT TAT GGA AAT TTC TAC GCT ATG GAT TAT TGG GGA CAA GGT ACA TCT GTT ACT GTG
CCA GGA ATA CCT TTA AAG ATG CGA TAC CTA ATA ACC CCT GTT CCA TGT AGA CAA TGA CAC
```

TABLE 3-continued

Sequence of T-5.91 scFv (nico)

```
  S   S   G   G   G   G   S   G   G   G   G   S   G   G   G   G   S   D   I   Q
TCC TCT GGA GGT GGA GGT TCT GGA GGT GGA GGT TCA GGA GGT GGA GGT AGT GAT ATT CAA
AGG AGA CCT CCA CCT CCA AGA CCT CCA CCT CCA AGT CCT CCA CCT CCA TCA CTA TAA GTT

M   T   Q   S   P   A   S   L   S   A   S   V   G   E   T   V   T   I   T   C
ATG ACA CAG TCA CCT GCT TCA CTT AGT GCA TCC GTT GGT GAA ACT GTG ACA ATC ACT TGC
TAC TGT GTC AGT GGA CGA AGT GAA TCA CGT AGG CAA CCA CTT TGA CAC TGT TAG TGA ACG

R   A   S   G   N   I   H   N   Y   L   A   W   Y   Q   Q   K   Q   G   K   S
AGA GCT TCT GGA AAC ATA CAT AAC TAC TTA GCA TGG TAC CAA CAG AAG CAG GGT AAA TCA
TCT CGA AGA CCT TTG TAT GTA TTG ATG AAT CGT ACC ATG GTT GTC TTC GTC CCA TTT AGT

P   Q   L   L   V   Y   N   A   K   T   L   A   D   S   V   P   S   R   F   S
CCA CAG TTA CTC GTT TAC AAT GCT AAG ACA CTT GCA GAT AGT GTG CCT TCC AGG TTT TCT
GGT GTC AAT GAG CAA ATG TTA CGA TTC TGT GAA CGT CTA TCA CAC GGA AGG TCC AAA AGA

G   S   G   S   G   T   Q   F   S   L   K   I   N   S   L   Q   P   E   D   F
GGA TCA GGT AGT GGA ACT CAA TTC TCC CTC AAG ATT AAT AGT CTC CAG CCT GAG GAT TTT
CCT AGT CCA TCA CCT TGA GTT AAG AGG GAG TTC TAA TTA TCA GAG GTC GGA CTC CTA AAA

G   S   Y   Y   C   Q   H   F   W   S   T   P   Y   T   F   G   G   T   K
GGA TCT TAT TAC TGT CAG CAC TTC TGG TCT ACT CCT TAC ACA TTT GGT GGT GGA ACT AAA
CCT AGA ATA ATG ACA GTC GTG AAG ACC AGA TGA GGA ATG TGT AAA CCA CCA CCT TGA TTT

XhoI
                           ~~~~~~~

L   E   I   K   R   *
CTT GAG ATA AAG AGA TGA CTC GAG
GAA CTC TAT TTC TCT ACT GAG CTC
```

In Table 3, CDRs are shown in bold underlined font, while the linker between LH and LV is shown in bold italcs.

The foregoing is illustrative of the present invention, and is not to be construed as limiting thereof. The invention is defined by the following claims, with equivalents of the claims to be included therein.

---

That which is claimed is:

1. A recombinant monoclonal antibody, comprising:
    (i) a light chain (LC) variable region having at the respective complementarity determining regions 1, 2 and 3 (LC-CDR1, LC-CDR2 and CL-CDR3) thereof the amino acid sequences:

```
    (LC CDR1; SEQ ID NO: 3)
    RASGNIHNYL;

(LC CDR2; SEQ ID NO: 4)
    NAKTLAD;
    and (LC CDR3; SEQ ID NO: 5)
    FWSTPYT,
    ```

(ii) a heavy chain (HC) variable region having at the respective complementarity determining regions 1, 2 and 3 (HC-CDR1, CH-CDR2 and HC-CDR-3) thereof the amino acid sequences:

```
    (HC CDR1; SEQ ID NO: 8)
    GYTIH;

(HC CDR2; SEQ ID NO: 9)
    LINPYTGGITYNQNFKGKAT;
    and (HC CDR3; SEQ ID NO: 10)
    GPYGNFYAMDY,
    ``` wherein said recombinant monoclonal antibody or binding fragment thereof binds to IgE at an epitope corresponding to amino acids VDGQKATNIFPYTAPGTK (SEQ ID NO:11),
    wherein said recombinant monoclonal antibody is a single chain variable fragment (scFv), and
    wherein said recombinant monoclonal antibody or binding fragment thereof comprises a water soluble polyalkylene oxide group coupled thereto.

2. The recombinant monoclonal antibody or binding fragment of claim 1, wherein said recombinant monoclonal antibody or binding fragment binds to canine IgE at a dissociation constant ($K_d$) not greater than 50 nM.

3. A composition comprising said recombinant monoclonal antibody or binding fragment thereof of claim 1 in a pharmaceutically acceptable carrier.

4. The recombinant monoclonal antibody or binding fragment of claim 1, wherein the single chain variable fragment (scFv) forms an antigen-binding monomer.

5. The recombinant monoclonal antibody or binding fragment of claim 1, wherein said water soluble polyalkylene oxide group comprises polyethylene glycol.

6. The recombinant monoclonal antibody or binding fragment of claim 1, wherein said recombinant monoclonal antibody or binding fragment binds to canine IgE at a dissociation constant ($K_d$) not greater than 10 nM.

7. The recombinant monoclonal antibody or binding fragment of claim 1, wherein said recombinant monoclonal antibody or binding fragment binds to canine IgE at a dissociation constant ($K_d$) not greater than 1 nM.

8. The recombinant monoclonal antibody or binding fragment of claim 1, wherein the single chain variable fragment (scFv) is humanized, caninized, felinized or equinized.

9. A method of reducing free serum IgE levels in a mammalian subject in need thereof, comprising administering to said subject said recombinant monoclonal antibody or binding fragment of claim 1 in an amount effective to reduce free serum IgE levels in said subject.

10. A method of claim 9, wherein said subject is a dog, cat, or horse.

11. The method of claim 9, wherein said administering step is carried out by parenteral injection, topical administration, transdermal administration, oral administration, or inhalation administration.

12. The method of claim 9, wherein said subject is afflicted with atopic dermatitis, allergic rhinitis, allergic conjunctivitis, urticaria, gastro-intestinal inflammation, or oral-pharyngeal inflammation.

* * * * *

UNITED STATES PATENT AND TRADEMARK OFFICE
CERTIFICATE OF CORRECTION

PATENT NO. : 9,546,219 B2
APPLICATION NO. : 14/374679
DATED : January 17, 2017
INVENTOR(S) : Bruce Hammerberg Page 1 of 1

It is certified that error appears in the above-identified patent and that said Letters Patent is hereby corrected as shown below:

On the Title Page
Page 2, item (56), Other Publications, Please add the following reference at Line 8:
"Corren et al., Ann Allergy Asthma Immunol. 2004 Sep;93(3):243-8."

In the Specification
Column 20, Line 29: Please correct "(Fc ϵ RI)" to read -- (Fc ε RI) --

In the Claims
Column 33, Claim 1, Lines 21-28: Please correct the sequence below:

```
  (LC CDR1; SEQ ID NO: 3)
  RASGNIHNYL;

(LC CDR2; SEQ ID NO: 4)
  NAKTLAD;
  and (LC CDR3; SEQ ID NO: 5)
" FWSTPYT,                    " to read --
```
RASGNIHNYL (LC CDR1; SEQ ID NO:3);
NAKTLAD (LC CDR2; SEQ ID NO:4); and
FWSTPYT (LC CDR3; SEQ ID NO:5), and --

Column 33, Claim 1, Lines 36-43: Please correct the sequence below:

```
  (HC CDR1; SEQ ID NO: 8)
  GYTIH;

(HC CDR2; SEQ ID NO: 9)
  LINPYTGGITYNQNFKGKAT;
  and (HC CDR3; SEQ ID NO: 10)
" GPYGNFYAMDY,                " to read --
```
GYTIH (HC CDR1; SEQ ID NO:8);
LINPYTGGITYNQNFKGKAT (HC CDR2; SEQ ID NO:9); and
GPYGNFYAMDY (HC CDR3; SEQ ID NO:10), --

Signed and Sealed this
Fifteenth Day of August, 2017

Joseph Matal
*Performing the Functions and Duties of the
Under Secretary of Commerce for Intellectual Property and
Director of the United States Patent and Trademark Office*